(12) United States Patent
Ruhnke

(10) Patent No.: US 10,309,809 B2
(45) Date of Patent: Jun. 4, 2019

(54) APPARATUS FOR DETECTING STAGNANT WATER

(71) Applicant: Neoperl GmbH, Muellheim (DE)

(72) Inventor: Christof Ruhnke, Trebbin (DE)

(73) Assignee: Neoperl GmbH, Muellheim (DE)

( * ) Notice: Subject to any disclaimer, the term of this patent is extended or adjusted under 35 U.S.C. 154(b) by 0 days.

(21) Appl. No.: 15/798,847

(22) Filed: Oct. 31, 2017

(65) Prior Publication Data

US 2018/0052021 A1 Feb. 22, 2018

Related U.S. Application Data

(62) Division of application No. 14/978,600, filed on Dec. 22, 2015, now Pat. No. 10,184,814.

(30) Foreign Application Priority Data

Jan. 14, 2015 (DE) .................. 10 2015 100 457

(51) Int. Cl.
*G01F 1/05* (2006.01)
*F03B 13/10* (2006.01)
*E03C 1/10* (2006.01)
*G01N 33/18* (2006.01)
*F24D 17/00* (2006.01)
*G01F 1/00* (2006.01)

(52) U.S. Cl.
CPC .................. *G01F 1/05* (2013.01); *E03C 1/10* (2013.01); *F03B 13/10* (2013.01); *F24D 17/0073* (2013.01); *G01N 33/18* (2013.01); *E03C 2201/40* (2013.01)

(58) Field of Classification Search
CPC ..... G01F 1/05; G01F 1/00; E03C 1/10; E03C 1/02; E03C 1/00; F03B 13/10; F03B 13/00
USPC ....................................... 422/62, 68.1, 82.01
See application file for complete search history.

(56) References Cited

U.S. PATENT DOCUMENTS

| | | |
|---|---|---|
| 5,079,495 A | 1/1992 | Yasuo |
| 2007/0108056 A1* | 5/2007 | Nyberg .................. B01D 61/44 204/554 |
| 2009/0277516 A1* | 11/2009 | Winkler ............... G05D 7/0635 137/486 |
| 2011/0203364 A1 | 8/2011 | Staake et al. |
| 2014/0107835 A1* | 4/2014 | Biasi .................... B67D 1/0036 700/231 |
| 2014/0312253 A1 | 10/2014 | Gan |

FOREIGN PATENT DOCUMENTS

| | | |
|---|---|---|
| DE | 690 00 906 T2 | 6/1993 |
| DE | 44 10 993 A1 | 10/1995 |
| DE | 10 2005 060 890 A1 | 7/2006 |
| DE | 10 2007 009 007 A1 | 8/2008 |
| DE | 10 2008 039 272 A1 | 2/2010 |
| DE | 10 2014 104 393 A1 | 10/2014 |

(Continued)

*Primary Examiner* — Christine T Mui
(74) *Attorney, Agent, or Firm* — Fay Sharpe LLP

(57) ABSTRACT

An apparatus for detecting stagnant drinking water includes a generator for producing electrical energy, an energy store for storing that energy, a control and analysis unit which detects the charge state of the energy store and a signal transmitter which emits a signal depending on the charge state of the energy store.

14 Claims, 1 Drawing Sheet

(56) References Cited

FOREIGN PATENT DOCUMENTS

| | | |
|---|---|---|
| DE | 10 2014 018 590 A1 | 6/2015 |
| EP | 0 675 234 A1 | 10/1995 |
| EP | 2 762 646 A1 | 8/2014 |

* cited by examiner

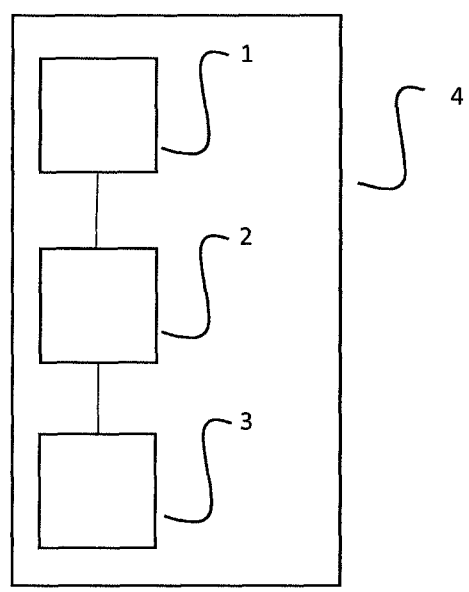

APPARATUS FOR DETECTING STAGNANT WATER

This application is a divisional application of U.S. patent application Ser. No. 14/978,600 which bears a filing date of Dec. 22, 2015 and is still pending.

BACKGROUND

The invention relates to an apparatus for detecting stagnant drinking water.

Stagnant water is to be understood as water which is stationary for a certain period of time in a pipe section. Stagnant water occurs when water is not removed (drawn off) for more than a certain period of time.

After only a few hours the formation of a biofilm can occur in stagnant water as a result of chemical, physical and microbial processes on the inner surface of the pipe section in question. Microbes, which multiply in a biofilm, reach the consumer when water is removed. A health risk to the consumer can result from this.

Pipe sections of e.g. faucets, conduits, shower hoses and tap outlets are affected by microbial contamination. In order to prevent or reduce microbial contamination in pipe sections, ring mains are known from the prior art from which relatively short feed lines go off to the water removal points. The advantage of such a construction is that when drawing off from each water removal point the water in the ring main is moved so that the residence time of the water in the ring main is low and stagnant water occurs only in the relatively short feed lines. The latter is vented by a flushing process before the drinking water (from the ring main) can be used. Ring mains are expensive and cannot be implemented universally.

Precautions can also be taken as regards materials which reduce microbial formation. In particular, materials are known from the prior art which reduce the risk of the formation of a biofilm.

The risk of using microbially contaminated drinking water can basically be reduced by allowing the water to run for a time before drawing off the drinking water provided for use. The pipe is thus flushed and potentially stagnant water discharged. Depending on the length of the water supply pipe, the running time of the water is up to a few minutes.

The method described above has proved in practice to be satisfactory. However, discharging unused water for a long period of time is environmentally unfriendly, particularly if, for reasons of safety, the water is discharged for longer than would actually be necessary.

Practice shows also that it is frequently not clear before using a drinking water tap connection whether the backed up water is stagnant water or not. The consumer frequently provides security by basically allowing the water to run for a relatively long period of time, regardless of the degree of stagnation of the water, before it is drawn off for its actual use. The result is unnecessary water wastage.

This is where the invention comes into play.

It is the object of the invention to detect stagnant water whilst simultaneously reducing unnecessary water consumption.

BRIEF SUMMARY

In order to solve this object, the above is characterised in accordance with the invention in that that electrical energy is produced in a pipe section by flowing water, that the electrical energy is stored in an energy store, that the charge state of the energy store is detected, and that information about possible stagnation of the drinking water is obtained from the charge state of the energy store.

The invention combines a number of advantages. One advantage resides in that electrical energy is produced by flowing water. No separate energy source is thus necessary. A further substantial advantage of the invention resides in the fact that information can be obtained from the charge state of the energy store as to whether stagnant water is present or not. In particular, the invention makes use of a discharged energy store in order to obtain the information from it that the water in the pipe section is stagnant water.

The energy store is preferably so selected that its discharge time is shorter than the time in which the water is considered subjectively or objectively to be stagnant water. The discharge time is, for instance, less than 12 hours, preferably less than 6 hours. Depending on the application, drinking water is defined as stagnant water when water is stationary on its travel in the pipe in question for longer than 4 hours. Such conditions are to be found, in particular, in medical installations, such as hospitals. Against this background, it can be convenient if the discharge time is less than 4 hours.

As indicated above, the invention can find application in public institutions, such as hospitals, residential homes for the elderly and care homes or schools and also in private households.

The degree of freshness of the drinking water is preferably derived from its stagnation. It is thus preferably possible that, on the one hand, it can be ensured that the water which is drawn off is fresh and that, on the other hand, unnecessary water is not wasted (by unnecessary flushing of the pipe).

It should be mentioned at this point that in the context of the invention the term degree of freshness is to be understood, for instance, merely as the states "fresh" or "not fresh". In a further embodiment of the invention, however, graduated degrees of freshness can also be determined. These are preferably derived from a partially discharged energy store. Thus when the energy store has a residual charge, it can be derived from this that the water which is drawn off is "not fresh".

The degree of freshness of the water is advantageously indicated acoustically and/or visually. The degree of freshness is thus rapidly ascertainable for the user. "Fresh" water can, for instance, be indicated with a light, which is e.g. green or blue. Additionally or alternatively, an acoustic signal or a series of acoustic signals can occur. With "not fresh", that is to say stagnant, water, there is preferably no acoustic and/or visual indication.

Alternatively and also regarded as advantageous is if stagnant water is indicated visually. There can, for instance, be a red signal. The water is thereby indicated as "fresh" if no signal is given. In this variant, a signal is thus a warning signal for stagnant water.

As soon as the water is stationary for a certain, preferably predetermined, period of time in the pipe section, the energy store discharges. If the pipe or pipe section is then flushed, the energy store charges up again. If the energy store is discharged, the drinking water is indicated as "fresh" after a certain, preferably predetermined, running time. In this connection, a number of scenarios are possible. For instance, the water is indicated as "fresh" when the energy store is fully charged or has reached a predetermined charge state. The pre-setting of a specific running time, for instance 1 minute, is also possible.

It is regarded as preferred if the running time is adjustable. The method is thereby matchable to its specific place of usage. If it is, for instance, known that the pipe section to the water removal point is long, the running time is selected to be long. With a short pipe section, for instance a short feed pipe, the running time can be maintained relatively short. As a result of the adjustability, the amount of flushing water, that is to say of stagnant water which is run off, can be maintained as small as possible. Such a water saving is environmentally friendly.

It can in practice be provided that the running time is continuously adjustable. Alternatively, the running time is adjustable in predetermined steps.

The adjustability described above offers a simple possibility of matching the method in accordance with the invention to environmental conditions. A certain knowledge of the location is thereby a prerequisite. More precise adjustability can be provided if, in order to determine the running time, water is permitted to run off once, the water temperature is measured during the running off process and the running off time is determined on the basis of the change in water temperature. The background to this possibility for adjustment is based on the fact that when the water is stationary its temperature matches the ambient temperature. This is, for instance, the temperature of the room through which the pipe in question runs. In north and west European countries, the room temperature is higher than the temperature of the "fresh" water coming from the central water supply. On the other hand, countries in warmer regions are known, in which the room temperature can be lower as a result of air-conditioning. As soon as a certain temperature change occurs, it can be inferred that fresh water is available at the removal point. In practice, the temperature measurement can be effected, for instance, manually, that is to say by feeling the temperature. As soon as the sensed water temperature subjectively changes, the time period is thus determined, after which the water is "fresh". The running of time thus determined can be used for future water removal processes.

As regards the energy store, those stores may be considered which store electrical energy and discharge within a suitable period of time. An accumulator can, for instance, be used. Since the discharge times of accumulators are long, as determined by their construction, additional electrical components, (such as, for instance, an optical indicator) can be provided, which are powered by the accumulator. The discharge time is thereby shortened.

It is considered to be particularly advantageous if the energy store is constructed in the form of a capacitor. Such capacitors can be maintained structurally very small. Furthermore, capacitors exhibit suitable charging and discharging characteristics.

The object is further solved by an apparatus for detecting stagnant water including
 a generator for producing electrical energy,
 an energy store for storing electrical energy,
 a control and analysis unit, which detects the charge state of the energy store, and
 a signal transmitter, which emits a signal in dependence on the charge state of the energy store.

The generator is preferably driven by a turbine. The turbine is advantageously a component of the apparatus. It is conveniently arranged in the pipe section.

The control and analysis unit detects the charge state of the energy store. The signal transmitter emits a signal in dependence on the charge state of the energy store. When the energy store is empty, the signal transmitter emits no signal. When the energy store is full, the signal transmitter preferably emits a signal, preferably one which shows the water to be "fresh".

The signal is advantageously an optical signal. The signal can be a permanent or a flashing light signal. It is, for instance, possible that "fresh" water is indicated by a first, for instance permanent, light signal. Depending on the discharge time of the energy store, stagnant water is indicated with a second light signal, for instance of a different colour. As explained above, when the energy store is discharged there is no signal, whereby it can additionally advantageously be provided that during the charging of the energy store, that is whilst water which is still stagnant is running off, a corresponding signal is emitted, which can be different to the first signal, which represents "fresh" water.

It is also regarded as advantageous when stagnant water is indicated and not "fresh" water. In normal operation, that is to say when "fresh" water is present at the removal point, there is advantageously no signal. When, however, the energy store is empty and stagnant water is removed, the electrical energy of the generator is used to emit a signal that the water is stagnant water. The signal is, for instance, red.

The apparatus in accordance with the invention is simple and composed of few components. It is considered to be particularly advantageous if the apparatus is in the form of an end or intermediate member for a water outlet, particularly for a water faucet. The apparatus in accordance with the invention can thus also be incorporated as a retrofit component. More substantial alteration of a standard faucet is not necessary for this purpose. In this connection, it is also advantageous if the energy store is constructed in the form of a capacitor which permits a particularly small overall size of the apparatus in accordance with the invention and its accommodation in the end or intermediate member.

In a further embodiment of the invention it is proposed that an input device is provided, by means of which the control and analysis unit can be supplied with a time period. The time period can be that time which the stagnant water requires to run out of a pipe section until it is fresh. With the energy store discharged, with an appropriate input into the control and analysis unit the water is only indicated as "fresh" after the time period. As explained above, the information relating to "fresh" water can be provided by an active (e.g. optical or acoustic) signal or by the fact that no signal is emitted. In the latter case, a signal is present when the water is stagnant water.

A temperature sensor can additionally be provided, which provides additional monitoring of the water. For instance, the stagnant water, which is running off, can be monitored as to whether, optionally after a pre-set time period, after a temperature change the water temperature is constant.

BRIEF DESCRIPTION OF THE DRAWINGS

The invention will be described in more detail below with reference to the attached drawing in conjunction with the described exemplary embodiment. The drawing shows:

FIG. 1: a schematic view of the basic construction of a detection apparatus in accordance with the invention.

DETAILED DESCRIPTION

The apparatus in accordance with the invention includes a generator 1, which is arranged in a pipe section (not shown). The generator 1 is driven by a turbine located in the pipe section through which water flows and thus produces electrical energy. The energy is stored in an energy store 2, which can be constructed, for instance, in the form of a capacitor. Reference numeral 3 designates a signal transmitter, which produces, for example, an optical signal when fresh water is at the tap connection. The components 1, 2 and 3 can be accommodated in a unit 4, which is, for instance, an end member or an intermediate member 4 for a water outlet.

The invention claimed is:

1. Apparatus for detecting stagnant drinking water, including
    a generator for producing electrical energy,
    an energy store for storing the electrical energy,
    a control and analysis unit, which detects a charge state of the energy store, and including
    a signal transmitter, which emits a signal depending on the charge state of the energy store, wherein the energy store is so selected that a discharge time of the energy store is shorter than a time period after which the drinking water is considered to be stagnant.

2. Apparatus as claimed in claim 1, wherein the signal is an optical signal.

3. Apparatus as claimed in claim 1, wherein the apparatus is constructed as an end member or an intermediate member for a water outlet.

4. Apparatus as claimed in claim 3, wherein the water outlet comprises a water faucet.

5. Apparatus as claimed in claim 1, wherein the energy store is constructed in the form of a capacitor.

6. Apparatus as claimed in claim 1, further comprising an input device, by means of which the control and analysis unit can be supplied with a time period.

7. Apparatus as claimed in claim 1, further including a temperature sensor.

8. An apparatus for detecting stagnant drinking water, including
    a water system unit;
    a generator for producing electrical energy;
    an energy store for storing the electrical energy;
    a control and analysis unit, which detects a charge state of the energy store, and including
    a signal transmitter, which emits a signal depending on the charge state of the energy store, wherein the energy store is so selected that its discharge time is shorter than a time period after which the drinking water is considered to be stagnant; and,
    wherein the generator, the energy store and the control and analysis unit are mounted to the water system unit.

9. The apparatus of claim 8, wherein the signal is an optical signal.

10. The apparatus of claim 8, wherein the water system unit comprises an end member or an intermediate member for a water outlet.

11. The apparatus of claim 10, wherein the water outlet comprises a water faucet.

12. The apparatus of claim 8, wherein the energy store comprises a capacitor.

13. The apparatus of claim 8, further comprising an input device, by means of which the control and analysis unit can be supplied with a time period.

14. The apparatus of claim 8, further comprising a temperature sensor.

* * * * *